United States Patent [19]

Kolchev

[11] 4,070,422

[45] Jan. 24, 1978

[54] METHOD FOR PRODUCING PHYTIN

[75] Inventor: Lyubomir Alexandrov Kolchev, Pleven, Bulgaria

[73] Assignee: DSO "UHARMACHIM", Sofia, Bulgaria

[21] Appl. No.: 721,841

[22] Filed: Sept. 9, 1976

Related U.S. Application Data

[63] Continuation-in-part of Ser. No. 543,917, Jan. 24, 1975, abandoned.

[30] Foreign Application Priority Data

Feb. 26, 1971 Bulgaria ................................. 16916

[51] Int. Cl.² ........................................... C07F 9/117
[52] U.S. Cl. ..................................... 260/990; 260/928
[58] Field of Search ............................... 260/990, 928

[56] References Cited

U.S. PATENT DOCUMENTS

| | | | |
|---|---|---|---|
| 2,170,274 | 8/1939 | Morgan | 260/928 X |
| 2,732,395 | 1/1956 | Bolley, et al. | 260/928 X |
| 3,591,665 | 7/1971 | Kimura, et al. | 260/928 X |

*Primary Examiner*—Anton H. Sutto
*Attorney, Agent, or Firm*—Armstrong, Nikaido & Marmelstein

[57] ABSTRACT

Protein and phosphorous free phytin is recovered from raw materials containing phytin by a process whereby the raw material is treated with an aqueous acid solution having a pH of about 1 to obtain a filtrate from which the phytin is precipitated by adding sufficient of a solution of bicarbonate ions to produce a pH of 7–8. In this way, phosphorous ions remain in solution while the phytin is precipitated out. The subsequently recovered precipitated phytin is again dissolved in a mineral acid and then saturated with a denaturating agent such as sulfur dioxide, ether or formaldehyde to thereby eliminate protein from the solution. Upon the addition of sufficient alkaline agent, the phytin is again precipitated and recovered in its purified form.

3 Claims, No Drawings

METHOD FOR PRODUCING PHYTIN

This is a continuation-in-part application of U.S. patent application Ser. No. 543,917, filed Jan. 24, 1975 now abandoned.

The present invention relates to a method for producing phytin from raw materials containing phytin particularly from different sorts of groats, rice brans and other wastes of the food industry.

One known method for obtaining phytin acid from phytin containing inorganic phosphorous is disclosed in U.S. Pat. No. 3,591,665 and consists of extracting phytin from waste raw materials with solutions of hydrochloric acid, sulphuric acid or acetic acid, precipitating the phytin with ammonia, sodium hydroxide or potassium hydroxide, purifying it from organic protein solvents or inorganic salts with ammonia solution at pH 9.2, washing the phytin with distilled water at 50° C for an hours and washing and filtrating three times. The phytin obtained contains inorganic phosphorous. According to this method a 0.50% sulphuric acid is used which has a pH 1, and at the end of the extraction the pH is about 3 and the isoelectric point of the proteins is not reached.

It is also known from U.S. Pat. No. 2,732,395 to extract phytin from seeds. The phytin extraction is performed with hydrochloric acid at pH 4.5–4.9 and product sedimentation at pH 6.4–7. For the sedimentation of phytin, the alkalization of the extract is carried out with 5% alkaline solution while the sedimentation of technical phytin is achieved by boiling the neutralized solution at pH 7 for 1.5 hours. After the extraction of the phytin, the proteins are extracted from the solid fraction with sodium hydroxide solution at pH 11 and from this solution when pH is reduced to 4.7, the protein is coagulated and forms a sediment. As can be seen from the cited patent tables of the proteins and phytin percentage, the fact that the protein extraction is performed in a separate method stage at pH 11 and then the protein is coagulated with sulphur dioxide, results in obtaining phytin mixed with protein and protein containing phytin. This is because sulphur dioxide is used only for protein sedimentation but not for destroying of the "phytin-protein complex". Therefore, it is characteristic of prior aret methods of obtaining phytin that the product is not sufficiently pure. The most difficult problem in obtaining pure phytin is the purification of proteins and inorganic phosphates which are invariably found in it.

Baking powder is also known in (U.S. Pat. No. 2,170,274) which contains 15–40% phytin acid, 26–60% sodium bicarbonate and the remaining part starch. The baking powder produces not less than 12% carbon dioxide. Another baking powder is known which has alkaline phytates as an acid agent. In this case, the ingredient, sodium bicarbonate, is used only for obtaining of carbon dioxide. And, not for sedimenting of phytin and converting the inorganic phosphates into dissoluble phosphates.

An object of the present invention is to provide a method for producing phytin that would ensure the production of a pure pharmaceutic product, the method being sufficiently cheap and profitable. The essential features of the method according to the invention are that the raw materials containing phytin are extracted with an aqueous solution of an acid, the phytin is precipitated from the acid extract by treating with a solution containing bicarbonate ions, then the phytin is separated by filtration, it is dissolved in a mineral acid, an agent for denaturating the proteins is added, preferably sulphur dioxide, ether or formaldehyde as well as kieselguhr and after filtrating the acid filtrate, phytin is precipitated by treatment with an alkaline salt. The isolating of phytin is achieved by means of known methods of filtrating, washing and drying.

The novelty of the method consists first of all in the fact that as a precipitating agent, solutions containing bicarbonate ions are used and as a result, soluble inorganic phosphate remains in the solution. Thus, they are eliminated from phytin, this being not possible in using the other precipitating agents known until up to now. Then a saturation with sulphur dioxide of the phytin solution is effected within determined limits so that the accompanying proteins coagulate and their destruction from the phytin-protein complex is attained. Furthermore, the sulphur dioxide acts as a bleaching agent, being of importance to the end color of the finished product. Ether and formaldehyde act also as denaturating agents.

The raw material containing phytin is extracted with an aqueous solution of an acid having a pH 1. Typically, about 5 parts by weight of 0.1 N acid at a pH of 1 to 1 part by weight of the raw material is employed. The acid extract when treated with a solution containing bicarbonate ions gives a precipitate of phytin at pH 7–8. This eliminates the precipitation of inorganic phosphates because insoluble $Mg(HCO_3)_2$ and $Ca(HCO_3)_2$ are obtained according to the following equation:

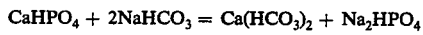

$$CaHPO_4 + 2NaHCO_3 = Ca(HCO_3)_2 + Na_2HPO_4$$

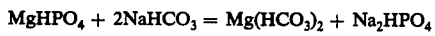

$$MgHPO_4 + 2NaHCO_3 = Mg(HCO_3)_2 + Na_2HPO_4$$

The phytin is separated by filtration and is dissolved in a mineral acid so that the resulting solution must have a pH 1. Then agents capable of destroying "the phytin-protein complex", e.g. $SO_2$, ether, formaldehyde are added and for better filtration at the end kieselguhr is added. From the acid filtrate after the filtration phytin is sedimented by treating with $NaHCO_3$ at pH 7–8. Further, the isolating of phytin is implemented by known techniques, i.e., through filtering, washing and drying. If agents for the destruction of the "phytin-protein complex" are not added, then this complex remains in the filter and the phytin therein precipitated is not purified but contains proteins.

The method according to the invention is illustrated by way of the following examples:

EXAMPLE 1

Into an extractor 2,500 l of 0.1 n hydrochloric acid was poured in order to extract 500 kg sun-flower groats, the average content of phytin in the raw material being approximately 3%. The mixer was set in operation and the groats were added in portions every 3 minutes. The extraction lasted 2 hours. The total amount of acid in relation to the groats was 5:1. The process was performed at room temperature with the pH of the suspension being 2 at the beginning and 4.7 at the end (which is the iso-electric point for protein) as determined by use of a universal indicator. Afterwards the suspension was centrifuged and the solid phase washed with water in relation 1:1. The juice along with the wash waters were collected in a tank-collector and then precipitated.

Precipitation was carried out with a solution of sodium bicarbonate 1:10. The purpose was to achieve a complete neutralization of the hydrochloric acid and to provide for an additional alkalinity. The pH of the solution was maintained at 7–8 until the complete precipitation of phytin, the precipitation process being carried out with continuous mixing. The complete precipitation lasted 4 hours. The liquor was decanted and the suspension of technical grade phytin was filtered through a nutsche-filter. The precipitate of technical grade phytin was then washed.

The technical grade phytin thus obtained in an amount of approximately 57 kg was dissolved in concentrated hydrochloric acid and the pH adjusted to 1 while mixing. To the solution was added 0.15% sulphur dioxide in relation to the volume and 6 l of 3% sulphurous acid. Then 15 g per 1 kieselguhr was also added. The suspension thus obtained, after mixing and settling was filtrated through a nutsch-filter. The filtration lasted 2 hours at room temperature. The precipitate was washed with water. The filtrate containing pure phytin was treated for the presence of proteins. The test tube containing 5 ml of the filtrate was diluted with 5 ml of distilled water, then 3 ml of ether sulphuricum ($C_2H_5OC_2H_5$) was added and the whole was vigorously shaken. Then it was left at rest unless separation of layers occurred. There was no protein ring between the water layer and the ether layer. From the filtrate is precipitated phytin by using a sodium bicarbonate solution. A precipitation of pure phytin was observed. The liquor was tested for its pH value and found to be 7 to 8. The precipitation of the pure phytin took 6 hours. The remaining suspension was filtrated through a nutsch-filter in vacuum. The pure phytin precipitate was dried in vacuum and then in a drier at temperatures from 60° C to 80° C during 6 hours. The dried product was controlled for its humidity content to not higher than 9%. The pure phytin obtained was tested for non-organic phosphates. To 0.10 g of phytin were added 2–3 drops of 2%($AgNO_3$). The sample was not colored yellow because of the action of $PO_4^{-3}$. The dried product was then ground in a mill and packed in a respective package. The technological yield of pharmaceutic grade phytin was 93% in relation to the initial phytin content in the raw materials, whereas its $P_2O_5$ content was 48.4%.

EXAMPLE 2

100 g rice brans with a phytin content of approximately 2% was extracted with 500 ml 0.1 N HCl at a pH of 1 for 2 hours. After filtrating and washing of the precipitate, the filtrate was precipitated with a sodium bicarbonate solution at a pH value of 7 to 8. The dried phytin was dissolved in 0.1 N solution of HCl in a concentration of 1:10. Then ether was added in an amount of 1:5 concentration to the volume of the solution and shook for 1 hour. The aqueous layer separated and from it was precipitated a pharmaceutic grade phytin with properties and a yield as in the case of Example 1.

EXAMPLE 3

To 100 ml of the suspension of a technical grade phytin in hydrochloric acid at pH 1 was added, instead of sulphur dioxide, 10 ml 40 percent formaldehyde. Then was added 15 g kieselguhr and it was agitated. After filtrating through a nutsch-filter from the filtrate was precipitated phytin satisfying the requirement of the Russian Pharmacopoea after the method described in Examiner 1.

EXAMPLE 4

100 g of soya groats were extracted with 500 ml of 0.1 N HCl at pH 1. At the beginning of the process the suspension had pH 2 and at the end — pH 4.7. The precipitate was filtered and washed. The filtrate together with the washing water was alkalized with a solution of $KHCO_3$ until pH 7–8 was reached, i.e., 50 ml of solution containing about 6 gr of $KHCO_3$ was added. The technical phytin obtained was dissolved in HCl to give a suspension of pH 1. Then 10 ml of 40% of formaldehyde and 1.5 g of kieselguhr were added and filtered. Then, the filtrate was tested for the presence of proteins as it is shown in Example 1. From the said filtrate after its dilution to 1 l with a solution of $KHCO_3$, pH 7–8, was precipitated pure phytin, free of proteins and inorganic phosphates.

EXAMPLE 5

100 g of wheat groats were treated to extract phytin under 500 ml of 0.1 N nitric acid for a period of 1 hour. The suspension was filtered and the remainder washed with water. The filtrate was alkalized with an equivalent quantity of potassium carbonate ($K_2CO_3$) i.e., about 6.8 g. Meanwhile, the reaction proceeded according to the equation:

$$HNO_3 + K_2CO_3 = KNO_3 + KHCO_3$$

to precipitate phytin free of inorganic phosphates. The phytin was further purified, as shown in Example 1.

What is claimed is:

1. A method for the production of inorganic phosphorus and protein free phytin from groats and rice brans containing phytin which comprises the steps of:
    a. forming a suspension of said raw materials and an aqueous solution of an acid selected from the group consisting of hydrochloric and nitric acid having a pH of about 1;
    b. filtering the suspension to obtain an acidified filtrate extract containing said phytin;
    c. adding an aqueous solution containing bicarbonate ions to said extract in an amount sufficient to produce a pH of 7–8 whereby phytin is precipitated;
    d. recovering the precipitated phytin;
    e. dissolving the recovered phytin in hydrochloric or nitric acid solution of pH 1;
    f. saturing the solution of phytin with a denaturing agent selected from the group consisting of sulfur dioxide, ether and formaldehyde;
    g. filtering the denatured solution to recover a solution of purified phytin free from protein; and
    h. precipitating the purified phytin by adding an aqueous bicarbonate solution to the solution thereof.

2. A method according to claim 1, wherein the suspension formed of groats and rice bran and said aqueous acid solution has an initial pH of about 2 and a pH at the end time of filtration of about 4.7.

3. A method according to claim 1, wherein the solution formed in step (g) is analyzed to determine the presence of proteins by extracting 5 ml of the solution and mixing it with 5 ml of distilled water and 3 ml of ether; shaking the mixture; allowing the mixture to separate into layers; and thereafter inspecting the interface between the layers for a protein ring.

* * * * *